United States Patent
Beek et al.

(10) Patent No.: US 9,861,755 B2
(45) Date of Patent: Jan. 9, 2018

(54) SPRING DRIVEN INJECTION DEVICE

(71) Applicant: Novo Nordisk A/S, Bagsvaerd (DK)

(72) Inventors: Willem van der Beek, Virum (DK); Steffen Hansen, Hilleroed (DK); Simon Roervig, Copenhagen (DK); Simon Munch Pedersen, Copenhagen (DK); Roger Harrington, Skaevinge (DK)

(73) Assignee: Novo Nordisk A/S, Bagsvaerd (DK)

( * ) Notice: Subject to any disclaimer, the term of this patent is extended or adjusted under 35 U.S.C. 154(b) by 148 days.

(21) Appl. No.: 14/435,845

(22) PCT Filed: Oct. 14, 2013

(86) PCT No.: PCT/EP2013/071451
§ 371 (c)(1),
(2) Date: Apr. 15, 2015

(87) PCT Pub. No.: WO2014/060369
PCT Pub. Date: Apr. 24, 2014

(65) Prior Publication Data
US 2015/0265776 A1    Sep. 24, 2015

Related U.S. Application Data

(60) Provisional application No. 61/716,731, filed on Oct. 22, 2012.

(30) Foreign Application Priority Data

Oct. 15, 2012  (EP) ..................... 12188471

(51) Int. Cl.
*A61M 5/315* (2006.01)
*A61M 5/20* (2006.01)
*A61M 5/31* (2006.01)

(52) U.S. Cl.
CPC .......... *A61M 5/31551* (2013.01); *A61M 5/20* (2013.01); *A61M 5/31515* (2013.01);
(Continued)

(58) Field of Classification Search
CPC .......... A61M 5/31551; A61M 5/31515; A61M 5/31593; A61M 5/20; A61M 5/31583; A61M 5/315
See application file for complete search history.

(56) References Cited

U.S. PATENT DOCUMENTS

2003/0050609 A1   3/2003  Sams
2006/0153693 A1*  7/2006  Fiechter ............ A61M 5/31553
                                          417/63

(Continued)

FOREIGN PATENT DOCUMENTS

JP    2010500893 A   1/2010
WO    2006076921 A1  7/2006
(Continued)

*Primary Examiner* — Bradley Osinski
(74) *Attorney, Agent, or Firm* — Wesley Nicolas

(57) ABSTRACT

The present invention relates to a torsion spring driven injection device for delivering multiple set doses of a liquid drug from a cartridge by moving a plunger forward inside the cartridge. The torsion spring (134) applies a rotational torque onto a drive member (120) engaging a piston rod (115) which is then driven forward by this rotation. The piston rod driver can be coupled and de-coupled from the torsion spring mechanism. In the de-coupled position, the piston rod driver is freely rotatable and can thus rotate if the piston rod is moved axially. A further torsion arrangement (124) is preferably provided such that a torque is build up between the piston rod driver and the housing whenever the piston rod is moved backwards. This torsion arrangement urges the piston rod driver to rotate in a direction bringing the piston rod forward into abutment with the plunger.

14 Claims, 8 Drawing Sheets

(52) U.S. Cl.
CPC .... *A61M 5/31553* (2013.01); *A61M 5/31583* (2013.01); *A61M 5/31593* (2013.01); *A61M 5/315* (2013.01); *A61M 5/3146* (2013.01); *A61M 2005/2013* (2013.01); *F04C 2270/0421* (2013.01)

(56) References Cited

U.S. PATENT DOCUMENTS

| | | |
|---|---|---|
| 2008/0306445 A1 | 12/2008 | Burren et al. |
| 2011/0054412 A1* | 3/2011 | Eich ........................ A61M 5/20 604/207 |

FOREIGN PATENT DOCUMENTS

| | | |
|---|---|---|
| WO | 2009101005 A1 | 8/2009 |
| WO | 2010029043 A1 | 3/2010 |
| WO | 2011023738 A1 | 3/2011 |
| WO | 2014001318 A2 | 1/2014 |
| WO | 2014001319 A1 | 1/2014 |

* cited by examiner

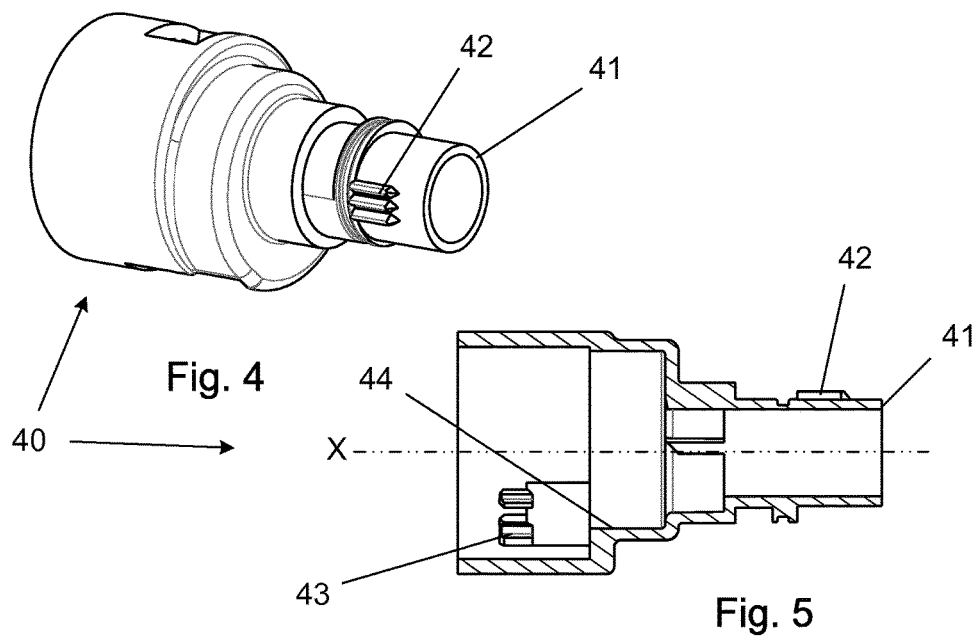
Fig. 4
Fig. 5
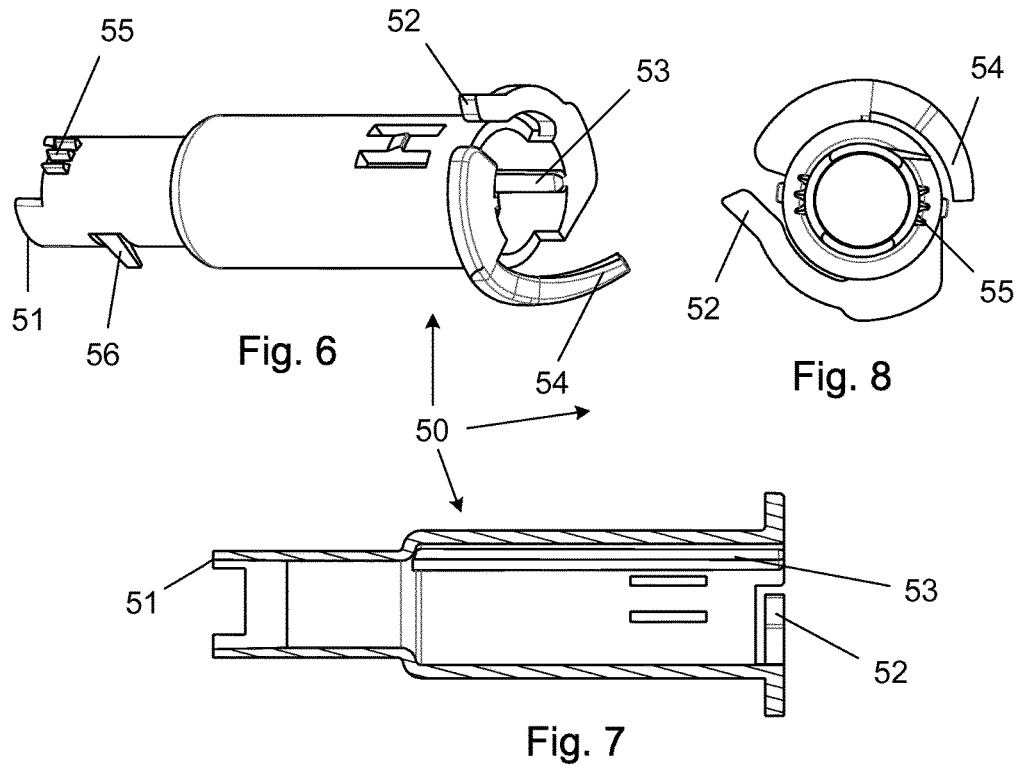
Fig. 6
Fig. 7
Fig. 8

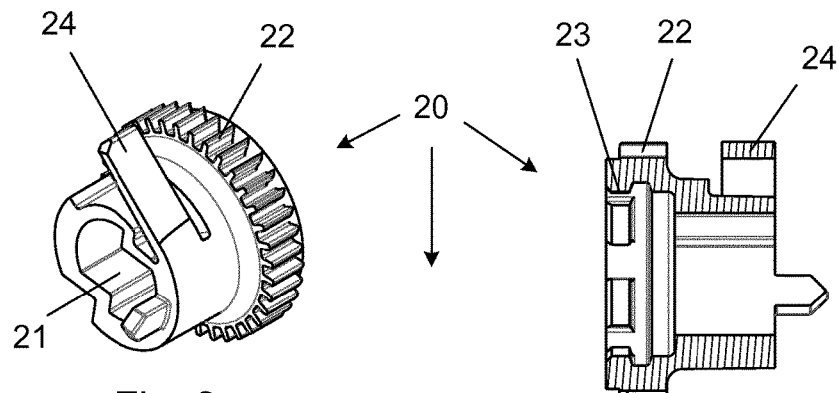
Fig. 9
Fig. 10
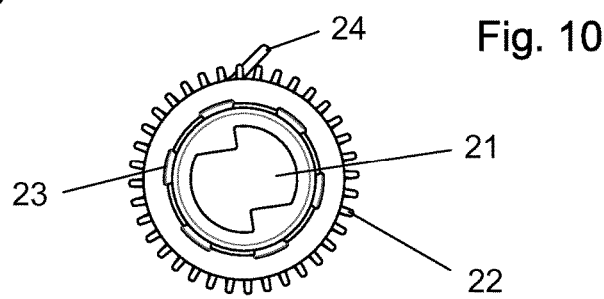
Fig. 11
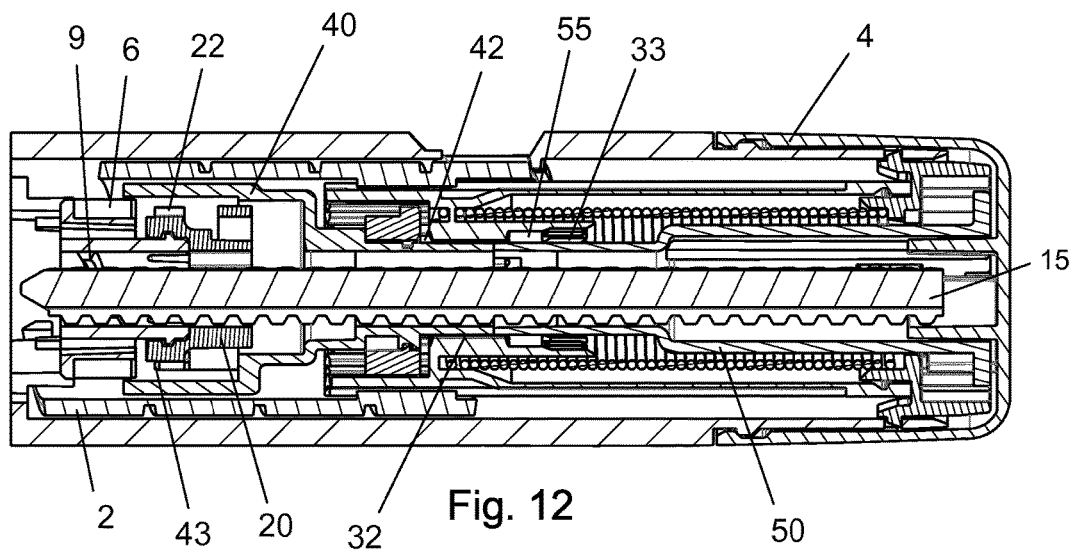
Fig. 12

SPRING DRIVEN INJECTION DEVICE

CROSS-REFERENCE TO RELATED APPLICATIONS

This application is a 35 U.S.C. §371 National Stage application of International Application PCT/EP2013/071451 (published as WO 2014/060369), filed Oct. 14, 2013, which claims priority to European Patent Application 12188471.2, filed Oct. 15, 2012; this application claims priority under 35 U.S.C. §119 to U.S. Provisional Application 61/716,731; filed Oct. 22, 2012.

THE TECHNICAL FIELD OF THE INVENTION

The invention relates to a torsion spring driven drug delivery device for delivering multiple individual set doses of a liquid drug. The drug delivery device is preferably of the type in which a drive member during dose ejection is rotated by a torsion spring to move a piston rod forward inside a cartridge. The invention more specifically relate to the coupling and decoupling of the drive member with the spring drive mechanism.

DESCRIPTION OF RELATED ART

Automatic torsion spring driven injection devices are widely known and have previously been thoroughly described in e.g. PCT application No.: PCT/EP2013/063249, PCT/EP2013/063250 and in WO 2006/076921.

In the torsion spring driven injection devices disclosed in PCT/EP2013/063249 and PCT/EP2013/063250, the dose set by straining the torsion spring is released by the backward or retractive movement of the needle covering shield. This is often referred to as shield triggering.

In the torsion spring driven injection device disclosed in WO 2006/076921, the dose is also set by straining the torsion spring but released by the user pushing a button located at a proximal end of the injection device.

In one embodiment of WO 2006/076921 disclosed at FIG. 10, a rotatable drive member engages the not circular cross-section of a piston rod having a threaded outer surface. The threaded outer surface of the piston rod is threaded to an internal thread provided in the housing. When the rotatable drive member is rotated, the piston rod rotates with it and is thereby screwed axially forward in the internal thread of the housing in a helical movement. The rotatable drive member is rotated by the torque of the torsion spring through a spring drive arrangement which couples the torsion spring to the housing. The torque is build up when the torsion spring is strained during dose setting and thereafter fully or partly released during dosing.

In the non-dosing situation i.e. when the dose release button is not activated, the rotatable drive member is locked to the housing thereby immobilizing any axial movement of the piston rod.

A similar torsion spring driven injection device is disclosed in US2011/0054412. In this injection device, the driver is also coupled to the piston rod via a keyed engagement and the piston rod is threaded to the housing to be rotated distally when the driver is rotated. The driver is rotated by a spring drive arrangement which is coupled to the driver by an axial movement of a proximally located dose button. The axial movement of the dose button couples the coupling designated K2 and decouples the coupling designated K1 to thereby allow dispensing. When the dose button is not activated the driver is locked against rotation such that the piston rod cannot move, neither distally nor proximally.

Both during dosing and due to temperature differences pressure is build up in the liquid drug contained in the cartridge in the injection device. This pressure acts on the piston rod which is unable to move axially. Potentially, this non escapable exceeding pressure is only released when an injection needle is attached to the injection device with the result that liquid drug starts to flow out from the tip of injection needle upon mounting of the injection needle.

If a user leaves the injection device with an injection needle mounted on the injection device between injections the exceeding pressure can be relieved through the injection needle with the result that liquid drug will drip from the injection needle. Further, air can be sucked into the cartridge through the injection as a result of these temperature differences. The result often being that the rubber plunger inside the cartridge moves out of its abutment with the piston rod. It is therefore all ways recommended to prime a drug delivery device prior to making an injection such that air is removed from the cartridge and the piston rod abuts the rubber plunger inside the cartridge. This removal of air is also often referred to as air-shots or flow check.

Priming is usually done by holding the injection device in an upright position and expelling small doses until the air has been ejected and liquid drug starts to flow from the tip of the injection needle.

First time an injection device is used, it is often recommended to perform an initial priming as the tolerances during assembling of the injection device and filling of the cartridge often results in the injection device being initially delivered to the user with a gap between the piston rod and the rubber plunger of the cartridge. In order to move the piston rod into abutment with the rubber plunger initial priming is done usually following the same procedure as when performing normal air-shots.

Usually a piston rod foot is provided between the piston rod and the rubber plunger of the cartridge to distribute the injection pressure over a larger surface of the rubber plunger. This piston rod foot can be hinged to the piston rod or loosely mounted i.e. without being attached to the piston rod. It can also be moulded integrally with the piston rod.

In order to reduce the waste of the liquid drug contained in the injection device and to simplify the use of the device a reduction or an avoidance of both initial priming and air-shots between injections is to be preferred.

DESCRIPTION OF THE INVENTION

It is an object of the present invention to provide a mechanism in which initial priming and air-shots between injections can, at least partly, but preferably fully, be avoided.

It is further an object to provide a mechanism making it possible for the drug in cartridge to automatically relief any exceeding pressure being build inside the cartridge.

Such pressure can e.g. occur due to temperature changes or if the injection device is of the type wherein the injection needle is withdrawn from the cartridge at the end of injection, this can hinder the pressure inside the cartridge from settling.

The invention is defined in claim 1.

Accordingly, in one aspect of the present invention, a torsion spring driven drug delivery device for delivering multiple set doses of a liquid drug is provided.

This torsion spring injection device comprises:

A housing encapsulating the mechanical components including the cartridge containing the liquid drug. However, the cartridge can also be provided in a cartridge holder which is attached to the housing. The housing also encapsulates the torsion spring exerting the torque needed to expel the set dose.

A piston rod which has a threaded outer surface and a not circular cross-section, A rotatable drive member mating the not circular cross-section of the piston rod (or having an inner thread mating the outer thread of the piston rod), A nut member non-rotatable engaging the housing and having an inner thread mating the outer thread of the piston rod (or mating the not circular cross-section of the piston rod). This piston rod is moved axially forward inside the housing when the drive member is rotated relatively to the nut member. During the forward motion of the piston rod which can either be rotational or linear, the rubber plunger inside the cartridge is forced forward to expel the drug from the cartridge.

A spring drive arrangement which is rotated by the torsion spring to rotate the rotatable drive member to move the piston rod forward in the housing.

The rotatable drive member is secured or coupled to the spring drive arrangement by a clutch element which can move axially between a first position and a second position;

i) the first position being a position in which the rotatable drive member is disconnected from the spring drive assembly such that the drive member rotate independently of the spring drive assembly, and ii) the second position being a position in which the rotatable drive member is connected to the spring drive assembly such that the drive member and the spring drive assembly rotate together.

The drive member is rotational and can either be in a keyed or splined engagement with the piston rod, which piston rod is then threaded to the nut member, or the drive member can be in a threaded engagement with the piston rod which is then keyed or splined to the housing. In the first example, the piston rod rotates forward whenever the drive member is rotated. In the latter example, the piston rod is moved linearly forward without rotation when the drive member is rotated. The drive member is preferably one single member, but could alternatively be part of an assembly In the first position, when no injection is being performed, the drive member is disconnected from the spring drive assembly and can rotate as the piston rod moves axially.

If the piston rod is threaded to the nut member, the piston rod rotates when moved axially and the drive member rotates with the piston rod. In the second example in which the piston rod is keyed to the nut member, the piston rod moves axially without rotation, however the drive member rotates as it is threaded to the piston rod and axially locked.

In the second position, when an injection is being performed, the drive member is connected to the spring drive assembly such that the torque of the torsion spring rotates the drive member and thus moves the piston rod forward in one of the described ways.

The nut member can be moulded integrally with the housing or is can be a separate part which is locked to the housing i.e. unable to rotate relatively to the housing.

Since the drive member can rotate freely as the piston rod is moved axially between injections, any pressure build up in the liquid drug in the cartridge can be relieved. If a pressure is being build up inside the cartridge, the rubber plunger in the cartridge will be forced in the proximal direction thus also moving the piston rod foot and eventually the piston rod in the proximal direction. As the drive member is free to rotate in the first position, the drive member will simply rotate as the piston rod moves proximally thereby avoiding any pressure from being build up inside the cartridge.

During dosing which is e.g. shield triggered, the drive member is instantly locked to the spring drive assembly in its rotational position and the spring drive assembly is released such that the released torque of the torsion spring is transformed into a rotation of the drive member and thus distal movement of the piston rod.

The coupling of the drive member to the spring drive assembly is done via the clutch such that the clutch element in the first position non-rotatable engages the nut member thereby preventing the clutch element from rotating relatively to the housing and disengages the drive member and further disengages the spring drive assembly whereby the drive member can rotate independently of the spring drive assembly. When moving the piston rod axially in both directions in this first position, the drive member rotates both relatively to the housing and relatively to the nut member and to the clutch which in this position engages the nut member.

The engagement between the clutch element and the nut member is done via a toothed engagement, but could be envisage in a number of other ways.

In the second position, which is during dosing, the clutch element disengages the nut member and further couples to both the drive member and the spring drive assembly such that the spring drive assembly rotates both the clutch element and the drive member to perform an ejection. When, in the second position the torque of the torsion spring is released, the torque rotates the spring drive assembly and with it the drive member thus bringing forward the piston rod.

The clutch element engages the drive member via a first toothed engagement and further engages the spring drive assembly via a second toothed engagement, however other types of engagements could be envisage.

A torsion element such as a resilient arm or a torsion spring is connected to the drive member (or moulded integral with the drive member) such that the torsion element is strained as the drive member is rotated. The torsion element is preferably provided between the drive member and the clutch element such that the torsion element is strained during rotation of the drive member in the first position. However, the torsion element could alternatively be provided between the drive member and the housing or the nut member or in fact any element to which the drive member rotate relatively in the first position.

A torque is build up in the torsion element whenever the piston rod moves axially in the first, released position e.g. when pressure is build up in the liquid drug inside the cartridge. This torque will thus always return the drive member when the pressure in the liquid drug is relieved. If e.g. a pressure is build up in the drug, the piston rod will be moved proximally by this pressure. If the pressure for some reason decreases, the drive member will under the influence of the torsion element rotate backward toward its initial position and thus bring the piston rod forward.

In this way the piston rod e.g. via a piston rod foot, will always abut the plunger of the cartridge. By initial applying a torque onto the torsion element initial priming can be avoided since the piston rod would always be moved distally by this initial torque.

To further allow the drive member to rotate more than one full revolution an intermediate element can be provided between the drive member and the clutch element. The intermediate element is preferably coupled to the clutch element by a one-way coupling which allows the intermediate element to rotate more than one revolution in one direction but prevents rotation in the opposite direction. The intermediate element is preferably coupled to the drive member such that the allowed rotational direction is the one allowing the piston rod to move indefinitely in the proximal direction.

The intermediate element is preferably coupled to the drive member via a torsion element e.g. a leaf spring such that a torque is stored in the torsion element when the drive member is rotated. This torque is in an example used to rotate the drive member in the opposite direction such that the piston rod and e.g. the piston rod foot are automatically moved distally into abutment with the plunger inside the cartridge.

Hence, the intermediate element makes it possible for the piston rod to move indefinitely in the proximal direction during pressure increase whereas the distal movement of the drive member during pressure decrease is limited to the torque stored in the torsion element which is usually less than one full rotation of the drive member. This is because the pressure inside the cartridge is more likely to increase than to decrease. Usually the pressure only decreases due to temperature changes whereas several physical parameters (and also temperature) occurring during dose injection influences the pressure increase.

In a further embodiment the torsion element can be avoided by securing the piston rod directly to plunger. This is preferably done by applying a piston rod foot which is permanently attached to the plunger and further attached to the piston rod in a way allowing rotation between the piston rod foot and the piston rod but preventing axial displacement there between.

The piston rod foot can e.g. be glued or spiked to the plunger, or made integral with the plunger, whereas the coupling between the piston rod foot and the piston rod can be a conventional click coupling. This click coupling is preferably designed such that it is self-tightening in the axial direction meaning that no play is possible between the piston rod and the piston rod foot. This is e.g. done by having some flexibility in the coupling such that the coupling automatically tightens itself without any play when clicked together. Alternatively, the piston rod and the piston rod foot can be moulded as one integral element however this would prevent rotation between the piston rod and the piston rod foot making it a solution preferred only if the piston rod do not rotate during dose ejection.

What is important is that the piston rod is permanently coupled to the plunger such that any movement of the plunger in either axial direction is instantly transferred to an axial movement of the piston rod and thus a rotational movement of the drive member. It is thus not necessary to have a torsion element to drive the drive member in the pressure decreasing direction since the piston rod follows any axial movement of the plunger. In this solution, the piston rod can move indefinitely in both directions.

A resilient element urges the clutch element into the first position such that the drive member is free to rotate when no action is taken with the injection device.

In one example, the clutch element abuts a ratchet element on which the resilient element is provided. The resilient element could be any kind of spring means including a plastic spring moulded together with e.g. the ratchet element. The ratchet element then pushes the clutch element distally into the first uncoupled position.

During injection, the clutch element is moved into the second coupled position against the bias of the resilient element. The movement of the clutch is preferably axial and preferably proximally and follows the release of the injection mechanism which can be released either by the user activating an injection button or by a shield trigger mechanism. In the shield triggered configuration, the axial movement of the clutch also releases the torque of the spring drive assembly such that the coupling of the drive member and the release of the torque is done simultaneously.

Definitions

An "injection pen" is typically an injection apparatus having an oblong or elongated shape somewhat like a fountain pen for writing. Although such pens usually have a tubular cross-section, they could easily have a different cross-section such as triangular, rectangular or square or any variation around these geometries.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

The term "Needle Cannula" is used to describe the actual conduit performing the penetration of the skin during injection. A needle cannula is usually made from a metallic material such as e.g. stainless steel and connected to a hub to form a complete injection needle also often referred to as a "needle assembly". A needle cannula could however also be made from a polymeric material or a glass material. The hub also carries the connecting means for connecting the needle assembly to an injection apparatus and is usually moulded from a suitable thermoplastic material. The "connection means" could as examples be a luer coupling, a bayonet coupling, a threaded connection or any combination thereof e.g. a combination as described in EP 1,536,854.

The term "Needle unit" is used to describe one single needle assembly carried in a container. Such container usually has a closed distal end and an open proximal end which is sealed by a removable seal. The interior of such container is usually sterile such that the needle assembly is ready-to-use. Needle units specially designed for pen injections systems are defined in ISO standard No. 11608, part 2, and are often referred to as "pen needles". Pen needles have a front-end for penetrating into the tissue of a user and a back-end for penetrating into the cartridge containing the drug.

"Cartridge" is the term used to describe the container containing the drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

Using the term "Automatic" in conjunction with injection device means that, the injection device is able to perform the injection automatically without the user of the injection device delivering the force needed to expel the drug. The force is typically delivered by an electric motor or by a spring as herein described. The spring is usually strained by the user during dose setting. However, such springs are usually prestrained in order to avoid problems of delivering very small doses. Alternatively, the spring can be fully preloaded by the manufacturer with a preload sufficient to empty the drug cartridge through a number of doses. Typically, the user activates a latch mechanism e.g. in the shape of a button on the injection device to release the force accumulated in the spring when carrying out the injection. The release mechanism can also be coupled to a proximally located injection button.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which:

FIG. 4 show a perspective view of the clutch element.

FIG. 5 show a cross-sectional view of the clutch element.

FIG. 6 show a perspective view of the ratchet element.

FIG. 7 show a cross-sectional view of the ratchet element.

FIG. 8 show an end view of the ratchet element.

FIG. 9 show a perspective view of the piston rod driver.

FIG. 10 show a cross-sectional view of the piston rod driver

FIG. 11 show an end-view of the piston rod driver.

FIG. 12 show a cross-sectional view of the injection device with the piston rod driver in the second coupled position.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as their relative dimensions are intended to serve illustrative purposes only.

Figure 1:
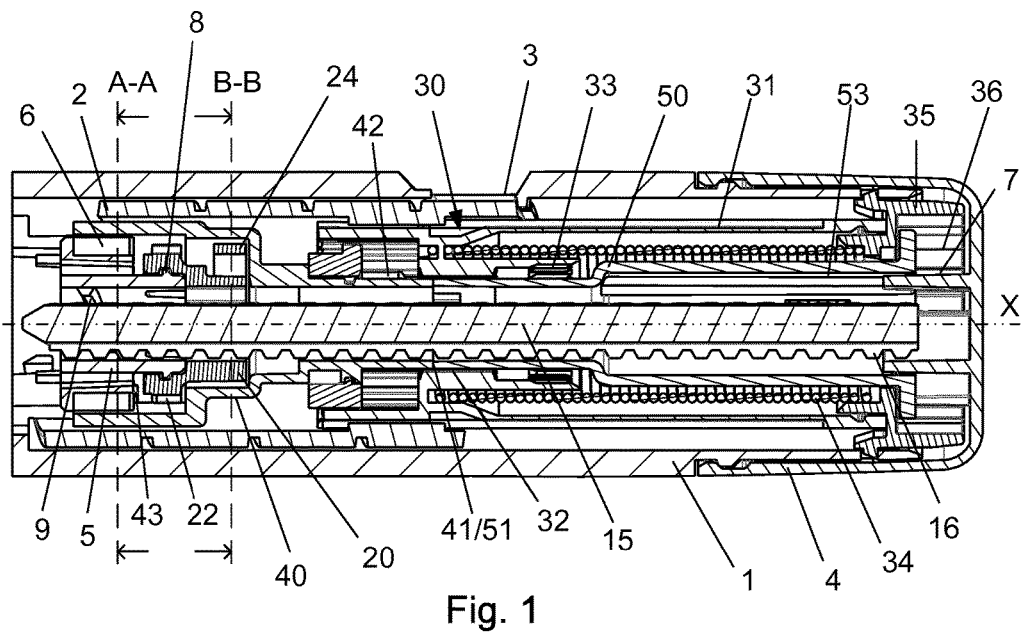
FIG. 1 show a cross-sectional view of the injection device with the piston rod driver in the first de-coupled position.

In that context it may be convenient to define that the term "distal end" in the appended figures is meant to refer to the end of the injection device which usually carries the injection needle whereas the term "proximal end" is meant to refer to the opposite end pointing away from the injection needle and carrying the dose dial button 4 as depicted in FIG. 1.

Some of the different components are only disclosed in relation to a single embodiment of the invention, but is meant to be included in the other embodiments without further explanation.

FIG. 1 discloses the injection device in the dose setting position ("first position") in which the piston rod driver 20 is disconnected from the spring drive assembly 30.

The basic elements of the injection device are:

A housing 1 encompassing the various components.

A scale drum 2, which visually informs the user of the dose size through a window 3 in the housing 1. The scale drum 2 is preferably threaded to the housing 1 and splined to the drive tube 31 such that it rotates with the drive tube 31 and performs a helical movement.

A dose setting button 4 which is rotatable mounted to the proximal end of the housing 1 and by which button 4 the user can set the dose to be injected.

A piston rod 15 for moving a plunger forward inside a cartridge containing the liquid drug in order to expel the set dose. The piston rod 15 is threaded 16 on its outer surface and further provided with a longitudinal extending track or similar not circular outer cross-section 17. Preferably, a piston rod foot is provided between the piston rod 15 and the plunger to distribute the forces applied from the piston rod to the plunger. This piston root foot is e.g. designated as "110" in FIG. 16.

A cartridge containing the drug to be expelled, the cartridge is mounted in the housing 1 or in a cartridge holder connected to the housing 1 distally to the piston rod 15 as in any injection device. The cartridge is designated "214" in FIG. 22.

The spring drive assembly 30 comprises the drive tube 31 and a torsion spring 34 which is positioned between the drive tube 31 and a spring base 35. The spring base 35 is firmly connected to the housing 1 in a non-movable manner, but could alternatively be moulded as a part of the housing 1. The torsion spring 34 is distally connected to the drive tube 31 such that the torsion spring 34 is strained when the drive tube 31 is rotated relatively to the housing and the spring base 35.

Figure 2:
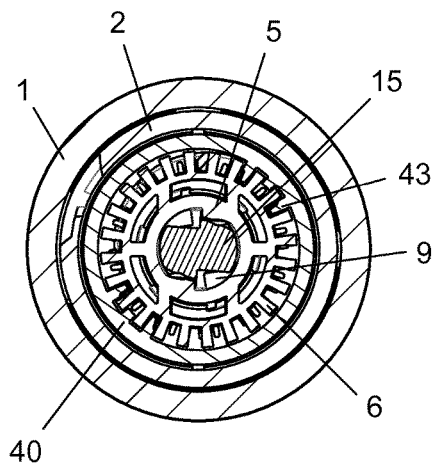
FIG. 2 show a view along the line A-A in FIG. 1.

FIG. 2 is a view through line A-A of FIG. 1 and discloses the nut element 5 which in the disclosed embodiment is moulded as a part of the housing 1 and has an internal thread 9 threadely engaging the outer thread 16 of the piston rod 15 such that the piston rod 15 is moved axially when rotated relatively to the nut element 5. The nut element 5 is externally provided with a plurality of external teeth 6.

Figure 3:
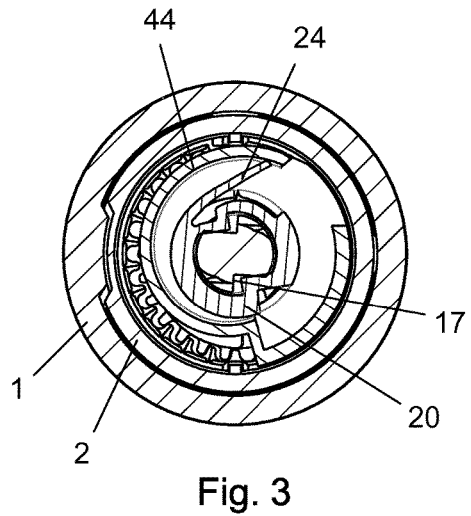
FIG. 3 show a view along the line B-B in FIG. 1.

FIG. 3 is a view through the line B-B of FIG. 1 providing a view of the engagement between the piston rod driver 20 and the clutch element 40 as will be explained later.

In FIG. 1, the proximal surface 41 of the clutch element 40 abuts the distal surface 51 of the ratchet element 50 (see FIG. 5 and FIG. 7). The clutch element 40 and the ratchet element 50 only abuts each other without any interconnection—the proximal surface 41 of the clutch element 40 simply just abuts the distal surface 51 of the ratchet element 50.

The piston rod driver 20 disclosed in FIG. 9-11 has a centre opening 21 which mates the non-circular cross section 17 of the piston rod 15 such that the piston rod 15 rotates whenever the piston rod driver 20 is rotated.

The clutch 40 is further depicted in FIG. 4 and FIG. 5. The clutch 40 is externally provided with a plurality of external teeth 42 and internally provided with a plurality of internal teeth 43, the function of which will be explained later.

The ratchet element 50 as disclosed in FIG. 6-8 is proximally provided with a ratchet arm 52 which engages an internal toothing 36 in the spring base 35. The ratchet element 50 is further provided with an internal ridge 53 which is splined to the dose setting button 4 through the track 7 provided internally in the dose setting button 4 (see FIG. 1) such that the ratchet element 50 rotates with the dose setting button 4.

A not-shown torque limiter can be provided between the dose setting button 4 and the ratchet element 50 such that the dose setting button 4 is able to continue rotation should the ratchet element 50 be prevented from rotation, which it e.g. is when no more drug is available in the cartridge. The torque limiter can e.g. be provided as either a part on the dose setting button 4 or a part on the ratchet element 50 being forced to move radially out of engagement when a certain torque is applied. An example of such torque limiter is provided in U.S. Pat. No. 5,921,966 (e.g. FIG. 6).

When a user sets a dose in the first position (FIG. 1), he rotates the dose setting button 4 which in turn rotate the ratchet element 50 via the track 7 and ridge 53 while the ratchet arm 52 clicks over the toothing 36 in the spring base 35. Distally the ratchet element 50 is provided with a set of external teeth 55 which engages similar teeth 32 inside the drive tube 31 such that the drive tube 31 is rotated together with the ratchet element 50 to strain the torsion spring 34.

The engagement between the ratchet arm 52 and the toothing 36 is designed such that the ratchet element 50 can only rotate in one direction relatively to the toothing 36 of the spring base 35, however, when rotating the dose setting button 4 in the opposite direction an element internally in the dose setting button 4 activates and releases the ratchet arm 52 from the toothing 36 of the spring base 35 thereby allowing the torsion spring 31 to rotate the ratchet arm 52 back to the previous teeth of the toothing 36. This "dial-down" mechanism is further explained in European patent application EP 2012 170139.

The ratchet element 50 is further provided with a spring arm 54 urging the ratchet element 50 in the distal direction relatively to the dose setting button 4 which the spring arm 54 abuts when moved proximally as will be explained later. The spring arm 54 could be replaced by a separate spring.

In the dose setting position as disclosed in FIGS. 1 and 2, the ratchet element 50 is urged in the distal direction and thus pushes the clutch element 40 also in the distal direction. In this position the internal teeth 43 inside the clutch element 40 engages the external teeth 6 of the nut member 5 thereby preventing rotation of the clutch element 40. As the user rotates the dose setting button 4 to select a dose, the distal surface 51 of ratchet element 50 rotates against the proximal surface 41 of the clutch element 40.

The external teeth 42 on the clutch element 40 are at the same time out of engagement with the drive tube 31 thereby allowing rotation of the drive tube 31 relative to the clutch element 40.

The internal teeth 43 of the clutch element 40 are, when engaging the nut member 5, out of engagement with the piston rod driver 20 which piston rod driver 20 is thereby allowed to rotate as nothing restricts rotational movement of the piston rod driver 20 in this first position.

The piston rod driver 20 (FIG. 9-10) has internally an opening 21 configured to mate the non-circular cross section 17 of the piston rod 15 and externally a toothed ring 22. Further the piston rod driver 20 is internally provided with snap arms 23 engaging a corresponding circular ridge 8 externally provided on the nut member 5. This allows the piston rod driver 20 to rotate relatively to the nut member 5 thus preventing it from moving axially.

As nothing, in this first position, prevents the piston rod driver 20 from rotating, it can rotate whenever the piston rod 15 is moved axially e.g. by the pressure inside the cartridge. This is referred to as pressure relief.

The piston rod driver 20 is on its outside surface provided with a spring arm 24 which abuts the inner surface 44 of the clutch element 40 as depicted in FIG. 3. This inner surface 44 is asymmetric such that the spring arm 24 is graduately urged towards the centre line X of the injection device 1 as the piston rod driver 20 is rotated, see e.g. FIGS. 3 and 5.

The result being that if the pressure inside the cartridge increases, the piston rod 15 will be moved axially in the proximal direction thereby imposing a rotation on the piston rod driver 20. If however the pressure inside the cartridge decreases, the abutment between the spring arm 24 and the asymmetric inner surface 44 of the clutch 40 will force the piston rod driver 20 to rotate in the opposition direction thus bringing the piston rod 15 distally forward. In other words; the engagement between the spring arm 24 and the asymmetric surface 44 operates as a torsional mechanism loading a torsional force into the spring arm 24 as it is rotated.

Alternatively, the spring arm 24 and the asymmetric surface 44 can be replaced by a torsion spring in which a torque is build when the piston rod driver 20 rotates relatively to the clutch 40. This will be explained later in connection with the second embodiment. Further, the spring arm 24 or the torsion spring can be fully avoided simply by connecting the piston rod to the plunger inside the cartridge such that the piston rod moves axially forth and back to follow the axial displacement of the plunger. This will also be explained in a later embodiment.

When a user injects the set dose, the clutch 40 is moved in the proximal direction into the position depicted in FIG. 12. The axial movement of the clutch element 40 can be performed in many different ways, one of which can be by a shield-trigger mechanism as disclosed in European patent application EP 2012 174289.

In this injection position (second position, FIG. 12), the clutch 40 moves the ratchet element 50 with it axially in the proximal direction against the bias of the spring arm 54. In this position, the internal teeth 43 of the clutch element 40 releases from the external teeth 6 of the nut member 5 which allows the clutch element 40 to rotate relatively to the nut member 5. At the same time the internal teeth 43 of the clutch element 40 engages the externally toothed ring 22 on the piston rod driver 20 such that the piston rod driver 20 rotates with the clutch element 40 when rotated.

The internal teeth 43 of the clutch element 40 have a shape that tappers towards the top of each teeth 43. This is best viewed in FIG. 2. In this way the somewhat broader rod (of the teeth 43) can engage the toothing 6 of the nut member 5 which in this example carries 24 individual teeth 6, whereas the narrower top can engage the toothed ring 22 of the piston rod driver 20 which also in this example carries 36 individual teeth 22.

The outer teeth 42 on the clutch element 40 engage with the similar teeth 32 provided internally on the drive tube 31 such that the clutch element 40 rotates together with the drive tube 31 in this second position. At the same time the external teeth 55 of the ratchet element 50 moves out of engagement with drive tube 31 thereby allowing the torsion spring 34 to rotate the drive tube 31 and together with it the clutch element 40 and the piston rod driver 20.

Alternatively, the teeth 32 can be provided as two independent circles of teeth, one circle proximally provided in the drive tube 31 and engaging with the teeth 55 of the ratchet element 50 in the first position and one circle distally provided in the drive tube 31 and engaging with the teeth 42 of the clutch element 40 in the second position.

Conclusively, to set a dose in the first position, the user rotates the dose setting button 4 which in turn rotate the ratchet 50 and the drive tube 31. During dose setting the torque of the torsion spring 34 is held by the ratchet arm 52. During dose setting, the clutch element 40 is in its distal position allowing the piston rod driver 20 to rotate independently while the clutch element 40 itself is locked to the nut member 5 and thus to the housing 1.

When a user wants to release the set dose, he moves the clutch element 40 axially and proximally which couples the clutch element 40 to the drive tube 31 which at the same time is released from the ratchet element 50 and set free to rotate under influence of the torque of the torsion spring 34. As the drive tube 31 and the clutch 40 rotate and the ratchet element 50 do not rotate since it is prevented from rotation by the ratchet arm 52, the click arm 56 produces a clicking sound against the internal toothing 33 provided internally in the drive tube 31, a clicking sound that corresponds to the dose being ejected. During the rotation of the clutch element 40, it is locked to piston rod driver 20 which then rotate the piston rod 15 to be screwed axially forward.

Figure 13:
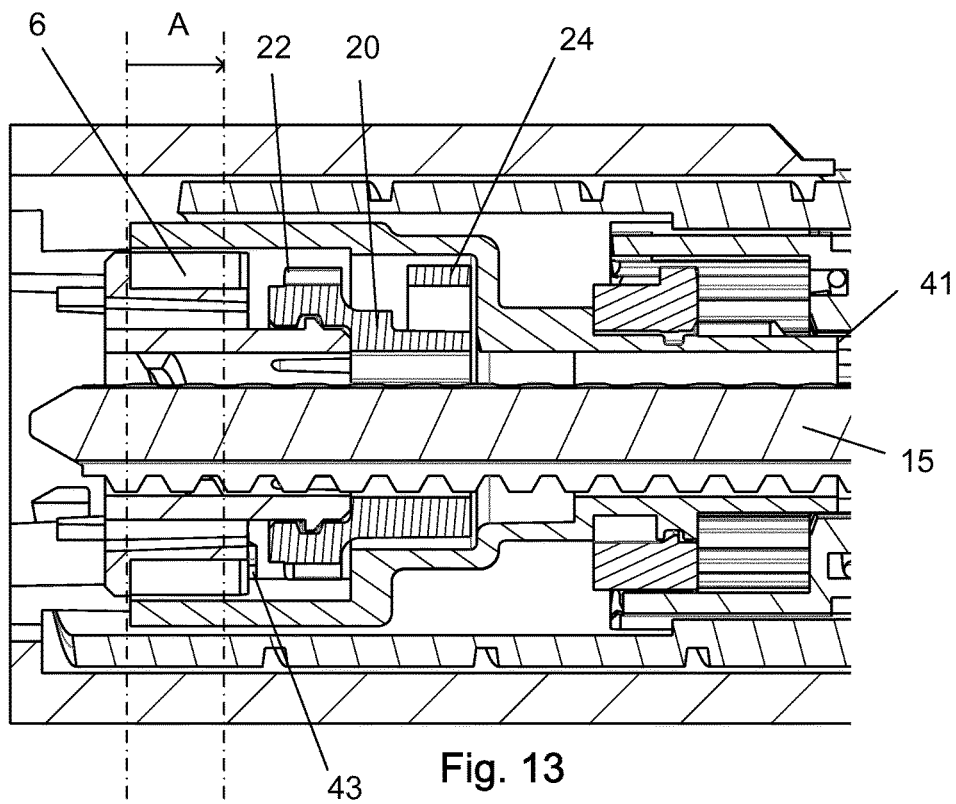
FIG. 13 show a close-up of the injection device of FIG. 1 i.e. in the de-coupled position.
Figure 14:
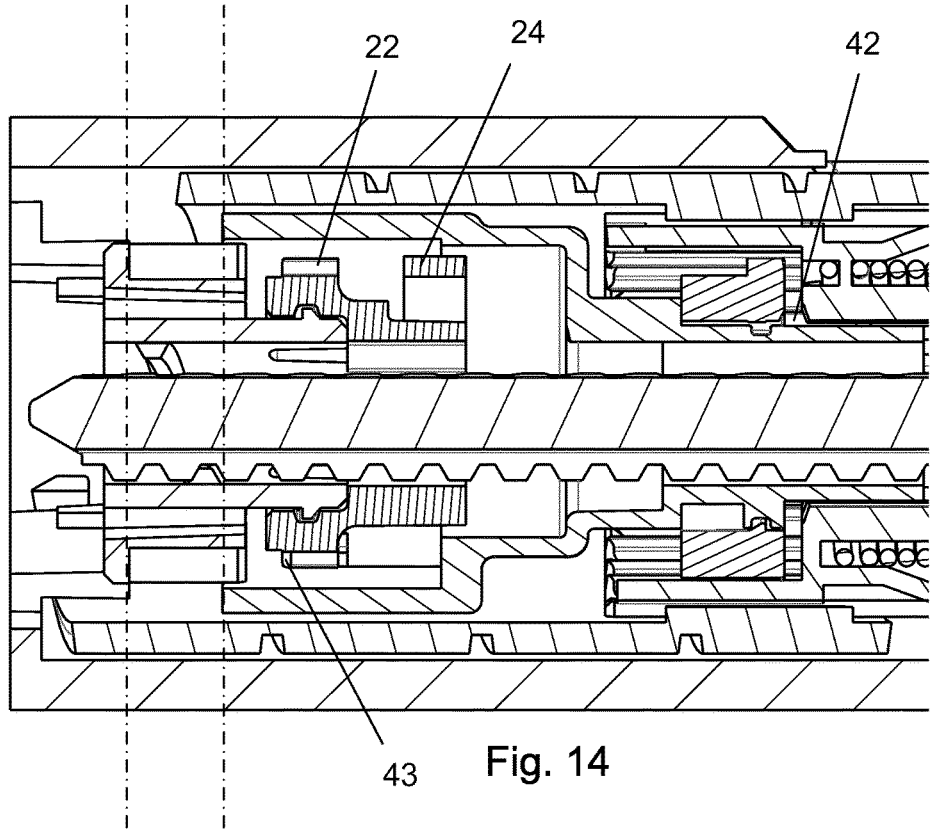
FIG. 14 show a close-up view of the injection device of FIG. 12 i.e. in the coupled position.

The first position is depicted in FIG. 13 and the second position is depicted in FIG. 14. The arrow A indicates the movement of the clutch 40. In the first position (FIG. 14) the piston rod driver 20 is free to rotate under the influence of the axial movement of the piston rod 15 and in the second position (FIG. 15), the piston rod driver 20 is locked to the clutch element 40 and rotates with the clutch element 40 which is released from the nut element 5 when the clutch is moved proximally thus rotating and moving the piston rod 15 forward in the threaded 9 nut member 5.

Figure 15:
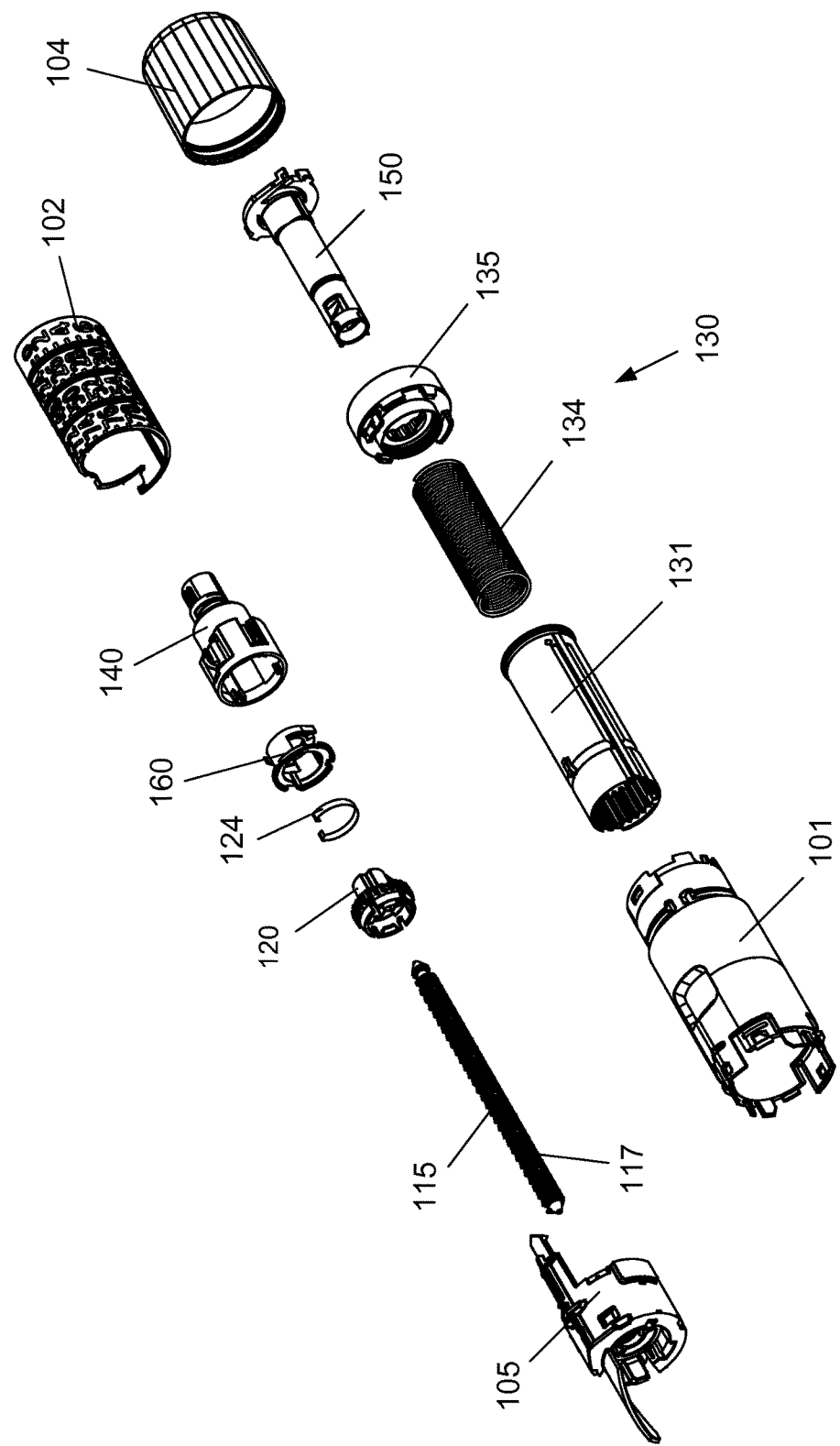
FIG. 15 show an exploded view of a different embodiment.

A slightly different embodiment is depicted in FIG. 15 which discloses an exploded view of the dose setting and injection mechanism also frequently referred to as the engine of the injection device.

The various elements are designated the same reference numbers as in the first embodiment (FIG. 1-14), however with a "1" in front. The main elements of the second embodiment are when moving from left to right across FIG. 15:

Nut member: 105
Piston rod: 115
Rotatable drive member: 120
Torsion element: 124
Clutch element: 140
Scale drum: 102
Housing: 101
Spring drive assembly 130, comprising:
Drive tube: 131
Torsion spring: 134
Spring base: 135
Ratchet: 150
Dose setting button: 104

Figure 16:
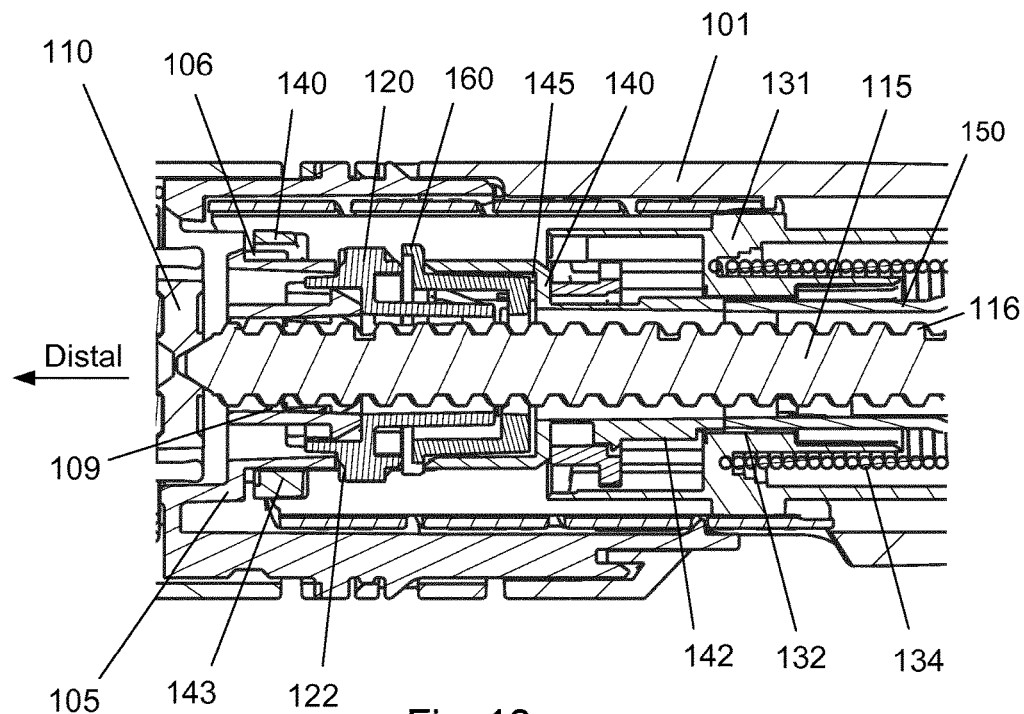
FIG. 16 show a cross-sectional view of the embodiment of FIG. 15 in the first de-coupled position.
Figure 17:
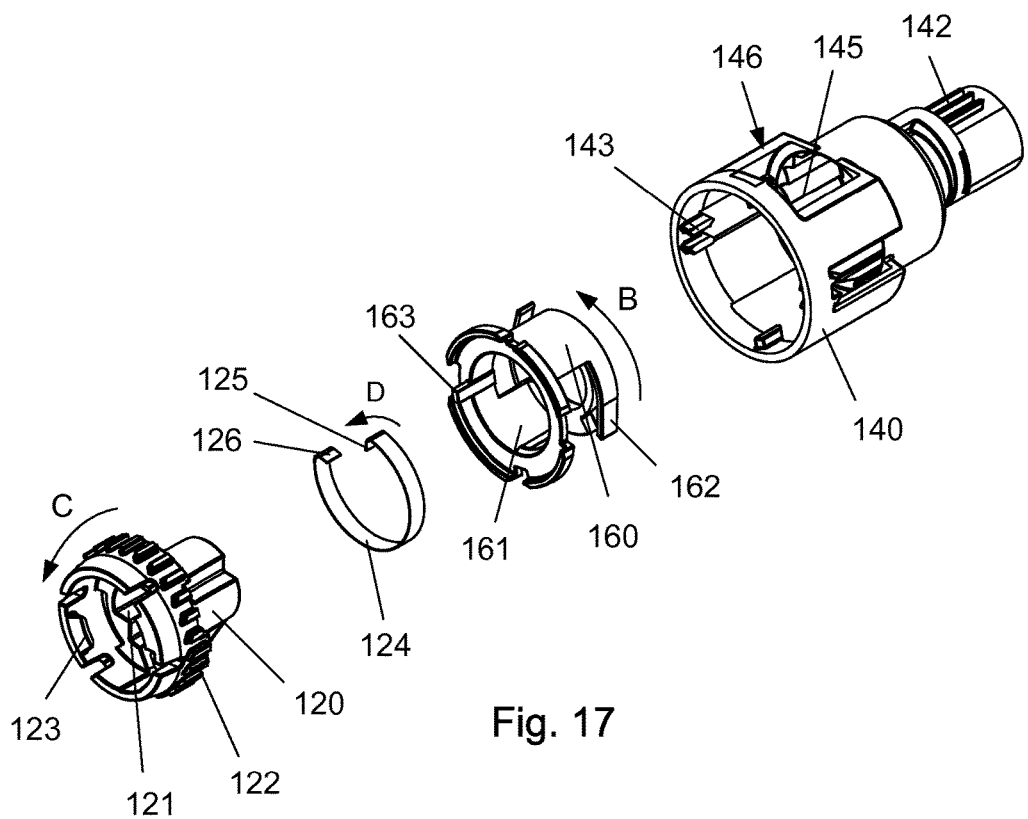
FIG. 17 show an exploded view of the main components of the pressure relief mechanism according to FIG. 15.

Further between the torsion element 124 and the clutch element 140 an intermediate element 160 is provided, which is the differentiating feature in this embodiment A cross sectional view of the mechanism in the first position is depicted in FIG. 16 and the relevant parts of the relief mechanism is further disclosed in an exploded view in FIG. 17. The clutch element 140 is distally provided with teeth 143 engaging similar teeth 106 provided on the nut element 5 such that the clutch element 140 in the first position is kept inrotatable relatively to the housing 101. The nut member 105 is in the disclosed example inrotatable coupled to the housing 101 (the nut member 105 and the housing 101 are fitted together via click means), but could alternatively be moulded as an integral component. Proximally the clutch element 140 is decoupled from the drive tube 131 as the teeth 142 is out of engagement with the teeth 132 of the drive tube 131.

Figure 20:
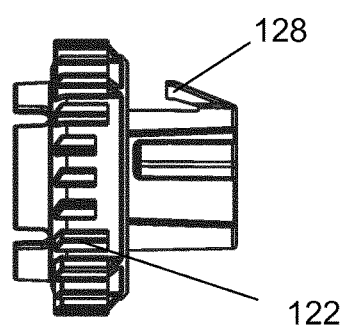
FIG. 20 show a side view of the piston rod drive of FIG. 17.
Figure 21:
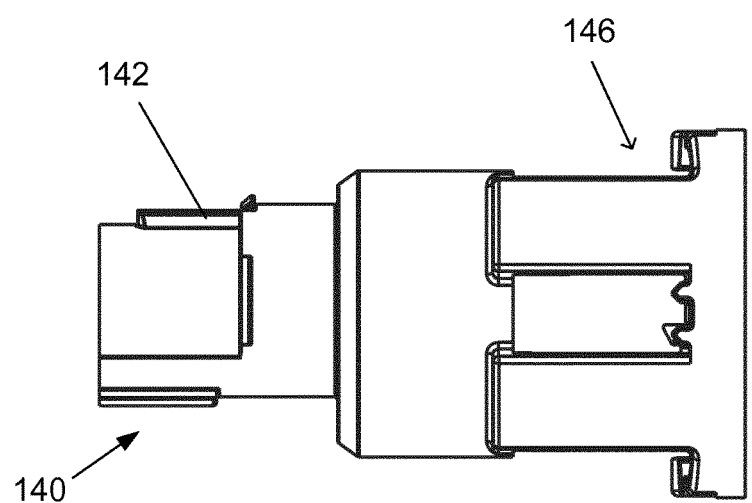
FIG. 21 show a side view of the clutch element of FIG. 17.

Please note that part of the clutch element 140 is not visible in the cross sectional view of FIG. 16 due to the cut-outs 146 indicated in FIGS. 17 and 20.

Further, in the first position, the drive member 120 is decoupled from the clutch element 140 such that the drive member 120 can rotate whenever the piston rod 115 is moved axially. The drive member 120 is coupled to the piston rod 115 via its centre opening 121 which mates the non-circular cross section 117 of the piston rod 115. As in the first embodiment the drive member 120 is axially locked to the nut member 105 by flexible arms 123 and the piston rod 115 is provided with an external thread 116 mating the internal thread 109 of the nut member 105.

In the second position (not disclosed), the clutch element 140 is moved axially in the proximal direction such that the teeth 143 disengages the teeth 106 of the nut member 105 and engages the teeth 122 of the drive member 120 and the teeth 142 engages with the teeth 132 provided internally in the drive tube 131 such that the drive member 120 in the second position follows the rotation of the drive tube 131. In the second position, the drive tube 131 rotates under influence of the torque of the torsion spring 134.

Figure 18:
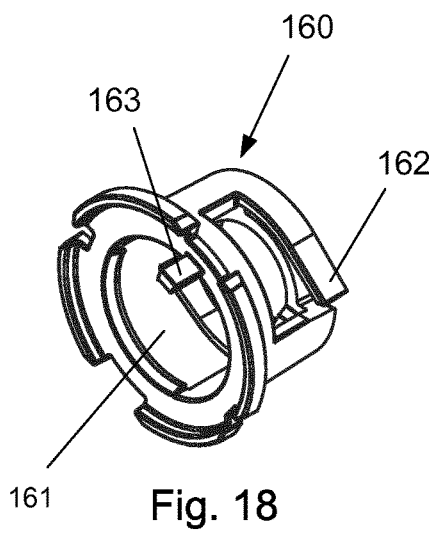
FIG. 18 show a perspective view of the intermediate element of FIG. 17.

The intermediate element 160 is provided between the drive member 120 and the clutch element 140. The intermediate element 160 which is further depicted in FIG. 18 has a centre opening 161 for obtaining a part of the drive member 120. Proximally the intermediate element 160 is provided with one or more ratchet arms 162 engaging a toothed surface 145 internally in the clutch element 140. This engagement restricts the intermediate element 160 to rotate in one direction only in relation to the clutch element 140. The allowed direction being counter clockwise when viewed from the distal end as indicated by the arrow "B" in FIG. 17. The individual teeth of the toothed surface 145 have a steep front preventing clockwise rotation of the intermediate element 160.

The torsion element 124 which in this second embodiment is embodied as a separate leaf spring having a first end 125 and a second end 126 is encompassed between the drive member 120 and the intermediate element 160. For that purpose, the intermediate element 160 is provided with a distally pointing arm 163 for holding the second end 126 of the torsion element 124.

Figure 19:
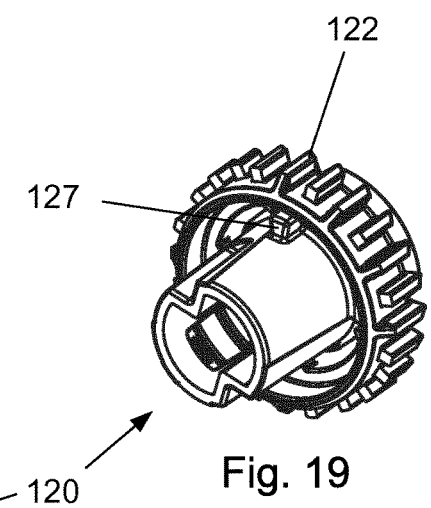
FIG. 19 show a perspective view of the piston rod drive of FIG. 17.

The drive member 120 depicted in FIG. 19 has a similar arm 127 for holding the first end 125 of the torsion element 124. As the drive member 120 and the intermediate element 160 is coupled together by the torsion element 124 and further connected by a small flexible arm 128 provided on the drive member 120, all three element 120, 124, 160 moves axially in unisome. To facilitate this, the axial length of the toothed surface 145 has a sufficient length to all ways be in engagement with the ratchet arms 162.

The working of the pressure relief mechanism is further explained with reference to FIG. 17. When the drug inside the cartridge expand and the plunger together with the piston rod foot 110 is moved proximally due to the increased pressure inside the cartridge, the drive member 120 is forced to rotate counter-clockwise as indicated by the arrow "C". This is due to the engagement of the non-circular cross section 117 of the piston rod 115 and the shape of the opening 121 in the drive member 120.

As the drive member 120 rotates counter-clockwise, the first end 125 of the torsion element 124 is also rotated counter-clockwise as indicated by the arrow "D" thereby tightening the torsion element 124. The ratchet arms 162 of the intermediate element 160 has a sufficient outward bend to withstand the torque applied to the torsion element 124 without moving to the subsequent tooth in the toothed surface 145 of the clutch element 140. However, when the first end 125 abuts the second end 126 of the torsion element 125 and the piston rod 115 keeps moving proximally the torque rises above a threshold value and the ratchet arms 162 jumps to the next subsequent tooth of the toothed surface 145 and remains in that position until the torque again raises beyond the threshold value created by the engagement between the ratchet arms 162 and the toothed ring 145.

In this way the piston rod 115 can move indefinitely in the proximal direction as there is no limit to the number of rotations the intermediate element 160 can perform in relation to the clutch 140.

If the pressure inside the cartridge decreases and the plunger move in the distal direction inside the cartridge, the torque of the torsion element 124 will automatically rotate the drive member 120 in the clockwise direction (opposite of the arrows "B", "C", "D") such that the piston rod 115 via the piston rod foot 110 will abut the plunger. In this clockwise direction, the intermediate element 160 is prevented from rotation due to engagement of the ratchet arms 162 with the toothed surface 145. The movement of the piston rod 115 in the distal direction is therefore limited to the possible rotation of the drive member 120 performed by the torque stored in the torsion element 124 which is in fact restricted to the gap between the first end 125 and the second end 126 of the torsion element 124. Once the torsion element 124 has resumed its initial configuration no more torque is present in the pressure relief mechanism.

Figure 22:
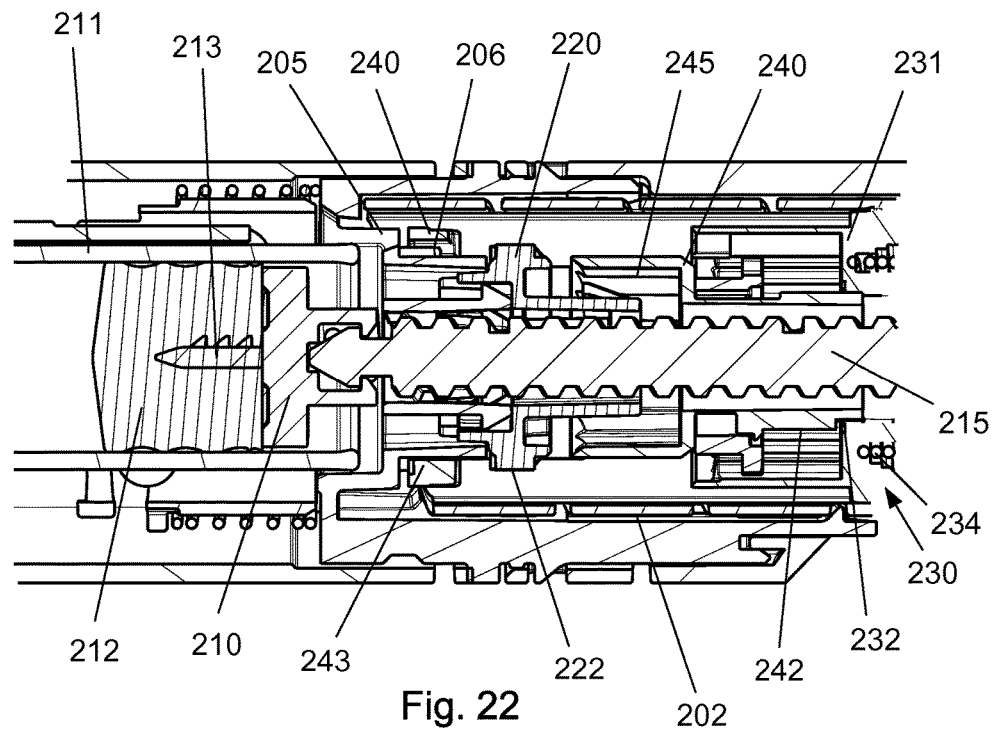
FIG. 22 show a further embodiment in the first de-coupled position.
Figure 23:
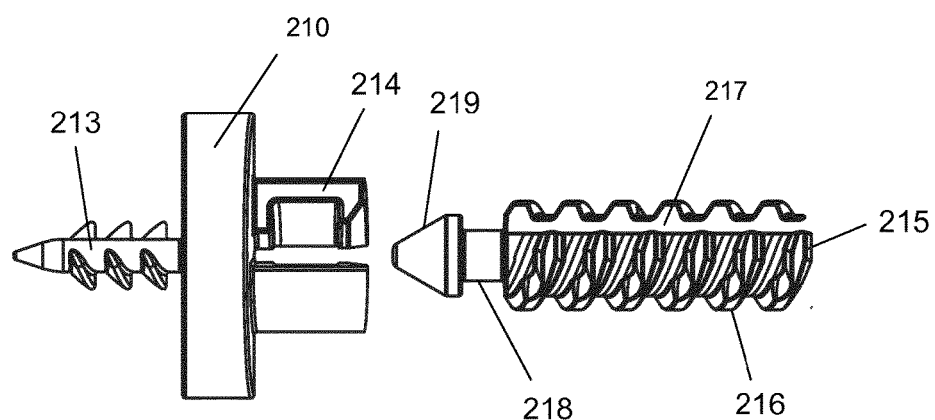
FIG. 23 show a side view of the piston rod and the piston rod foot of FIG. 22.

A third embodiment is disclosed in FIG. 22-23. In this third embodiment, the various elements are designated the same reference numbers as in the first embodiment (FIG. 1-14), however with a "2" in front of the reference number.

The main components being:
Nut member: 205
Piston rod: 215
Rotatable drive member: 220
Clutch element: 240
Scale drum: 202
Housing: 201
Spring drive assembly 230, comprising:
Drive tube: 231
Torsion spring: 234

The spring base and the dose setting button are not disclosed in FIG. 22 but are the same as in the previous embodiments.

Further, FIG. 22 also discloses the cartridge 211 with a plunger 212 which when moved forward by the piston rod 215 ejects the drug from the cartridge 210. A piston rod foot or washer 210 is provided between the piston rod 215 and the plunger 212.

FIG. 22 further discloses the clutch element 240 is the first position in which the teeth 243 of the clutch element 240 engages the teeth 206 of the nut member 205 and the teeth 242 of the clutch element 240 is disengaged from the teeth 232 of the drive tube 231.

The working principle is the same as in the previous embodiment. Once the clutch element 240 is moved proximally from its first position in FIG. 22 to its second position the teeth 243 of the clutch element 240 disengages the teeth 206 of the nut member 205 and engages the teeth 222 of the drive member 220. At the same time the teeth 242 of the clutch element 240 engages the teeth 232 of the drive tube 231 of spring drive assembly 230 such that the torque of the torsion spring 234 is transferred to a rotational movement of the clutch element 240 and consequently the drive member 220 which then moves the piston rod 215 axially in the distal direction.

The piston rod 215 is permanently fixed to the plunger 212 such that the piston rod 215 one-to-one follows any axial movement of the plunger 212 in the first position. Due to this engagement the torsion element between the clutch element 240 and the drive member 220 can be avoided since the piston rod 215 now automatically follows the plunger 212 in the distal direction when the pressure inside the cartridge 211 decreases. Therefore the internal toothing 245 of the clutch element 240 has no engaging counterpart in FIG. 22.

In the example, the plunger 212 is secured to a piston rod foot 210 which has a spike 213 inserted into the plunger 212.

This is further disclosed in FIG. 23 wherein the piston rod foot 210 distally is provided with a spike 213 and proximally with a number of flexible arms 214. The spike 213 is firmly inserted into the plunger 212 which is usually made from a rubber material. However the piston rod foot 210 and the plunger 212 could be permanently connected in many different ways e.g. by gluing or by welding the plunger 212 and the piston rod foot 210 together. Alternatively they could be moulded together e.g. by using a two-component moulding technique.

The piston rod 215 is as in the previous embodiments provided with an external thread 216 and a longitudinal track 217. Further a track 218 is provided at the distal end which snaps together with the flexible arms 214 such that the piston rod 215 and the piston rod foot 210 are axially locked but able to rotate in relation to each other. Opposite the track 218 the piston rod 215 can be provided with an inclined distal surface 219 which presses the piston rod foot 210 forward when the piston rod 215 and the piston rod foot 210 are connected to thereby reduce or preferably eliminate any play between the two parts 210, 215.

In the example in which the drive member 220 is splined to the piston rod 215 and the piston rod 215 is threaded to the nut member 205 the piston rod 215 rotates when moved axially. It is therefore, in that example, preferred if the piston rod 215 is rotatable mounted to the piston rod foot 210. In the other example, in which the drive member 220 is threaded to the piston rod 215 and the piston rod 215 is splined to the nut member 205, the piston rod 215 and the piston rod foot 210 could be moulded in one piece since as the piston rod 215 does not rotate during ejection in the latter example.

Some preferred embodiments have been shown in the foregoing, but it should be stressed that the invention is not limited to these, but may be embodied in other ways within the subject matter defined in the following claims.

The invention claimed is:

1. A torsion spring driven drug delivery device for delivering set doses of a liquid drug, comprising:
   A housing storing a cartridge containing the liquid drug and a torsion spring for exerting a torque,
   A piston rod having a threaded outer surface and a not circular cross-section,
   A rotatable drive member mating the not circular cross-section of the piston rod or having an inner thread mating the outer thread of the piston rod,
   A nut member non-rotatable engaging the housing and having an inner thread mating the outer thread of the piston rod or having a cross-section mating the not circular cross-section of the piston rod, such that the piston rod is moved axially forward in the housing when the drive member is rotated relatively to the nut member,
   A spring drive assembly which is rotatable by the torsion spring, positioned between the housing and the spring drive assembly, to rotate the rotatable drive member to move the piston rod forward in the housing, and
   wherein the rotatable drive member is coupled to the spring drive assembly by an axial movable clutch element which can move axially between a first position and a second position,
   i) in which the first position, when no injection is being performed, the rotatable drive member is disconnected from the spring drive assembly, wherein the clutch element disengages the drive member, and engages the nut member such that the drive member is rotatable independently of the spring drive assembly, thereby allowing proximal movement of the piston rod, and
   ii) in which the second position, when an injection is being performed, the rotatable drive member is connected to the spring drive assembly such that the spring drive assembly rotates the drive member to move the piston rod distally.

2. A torsion spring driven drug delivery device for delivering set doses of a liquid drug according to claim 1, wherein the clutch element engages the nut member via a toothed engagement.

3. A torsion spring driven drug delivery device for delivering set doses of a liquid drug according to claim 1, wherein the clutch element in the second position:
   disengages the nut member,
   engages the drive member, and
   engages the spring drive assembly.

4. A torsion spring driven drug delivery device for delivering set doses of a liquid drug according to claim 3, wherein the clutch element engages the drive member via a toothed engagement and further engages the spring drive assembly via a toothed engagement.

5. A torsion spring driven drug delivery device for delivering set doses of a liquid drug according to claim 1, wherein a torsion element is provided between the drive member and the clutch element which torsion element is strained during rotation of the drive member in the first position.

6. A torsion spring driven drug delivery device for delivering set doses of a liquid drug according to claim 5, wherein an intermediate element is provided between the rotatable drive member and the clutch element.

7. A torsion spring driven drug delivery device for delivering set doses of a liquid drug according to claim 6, wherein the intermediate element is coupled to the clutch element via a one-way coupling only allowing rotation of the intermediate element in one direction relatively to the clutch element.

8. A torsion spring driven drug delivery device for delivering set doses of a liquid drug according to claim 6, wherein the intermediate element is coupled to the drive member via the torsion element.

9. A torsion spring driven drug delivery device for delivering set doses of a liquid drug according to claim 8, wherein the torsion element comprises a torsional leaf spring provided between the drive member and the intermediate element.

10. A torsion spring driven drug delivery device for delivering set doses of a liquid drug according to claim 1, wherein the piston rod is secured to the plunger of the cartridge.

11. A torsion spring driven drug delivery device for delivering set doses of a liquid drug according to claim 1, wherein a resilient element urges the clutch element into the first position.

12. A torsion spring driven drug delivery device for delivering set doses of a liquid drug according to claim 11, wherein a ratchet element carries the resilient element and which ratchet element abuts the clutch element.

13. A torsion spring driven drug delivery device for delivering set doses of a liquid drug according to claim 12, wherein the clutch element is moved into the second position.

14. A torsion spring driven drug delivery device for delivering set doses of a liquid drug according to claim 13, wherein the clutch element is moved axially in the proximal direction during dose ejection.

* * * * *